US012176088B2

(12) United States Patent
Utech et al.

(10) Patent No.: US 12,176,088 B2
(45) Date of Patent: *Dec. 24, 2024

(54) SYSTEM AND METHOD FOR MONITORING PROGRESS OF DELIVERY OF A MEDICAL OBJECT

(71) Applicant: CareFusion 303, Inc., San Diego, CA (US)

(72) Inventors: Thomas Utech, San Diego, CA (US); Cynthia Yamaga, Oceanside, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/467,646

(22) Filed: Sep. 14, 2023

(65) Prior Publication Data

US 2024/0006043 A1  Jan. 4, 2024

Related U.S. Application Data

(63) Continuation of application No. 17/713,193, filed on Apr. 4, 2022, now Pat. No. 11,763,925, which is a
(Continued)

(51) Int. Cl.
| | |
|---|---|
| *G16H 20/13* | (2018.01) |
| *G06K 7/10* | (2006.01) |
| *G06K 7/14* | (2006.01) |
| *G06Q 10/0833* | (2023.01) |
| *G16H 10/60* | (2018.01) |

(Continued)

(52) U.S. Cl.
CPC ......... *G16H 20/13* (2018.01); *G06K 7/10386* (2013.01); *G06K 7/1408* (2013.01);
(Continued)

(58) Field of Classification Search
CPC ........ G16H 20/13; G16H 10/60; G16H 20/10; G16H 20/17; G16H 40/20; G16H 40/40;
(Continued)

(56) References Cited

U.S. PATENT DOCUMENTS

| | | |
|---|---|---|
| 6,094,642 A | 7/2000 | Stephenson et al. |
| 7,672,859 B1 | 3/2010 | Louie et al. |

(Continued)

FOREIGN PATENT DOCUMENTS

| | | |
|---|---|---|
| EP | 2315105 A1 | 4/2011 |
| KR | 1020000059084 | 10/2000 |

(Continued)

OTHER PUBLICATIONS

English language Office Action for United Arab Emirates Application No. UAE/P/0844/2013, mailed Jun. 22, 2017, 11 pages.
(Continued)

*Primary Examiner* — Tuyen K Vo
(74) *Attorney, Agent, or Firm* — Morgan, Lewis & Bockius LLP

(57) ABSTRACT

A reader device is configured to wirelessly read medical information from a medical identification device and location information from a location identification device when the devices are within a range of the at least one reader device. A tracking device receives an indication that first medical information and first location information was read at a first location when a first medical identification device associated with the first medical object and a first location identification device associated with the first location was read at the first location by at least one reader device, and a last-known location of the first medical object associated with the medical identification device is generated based on the first location information read at the first location. In response to receiving a tracking request for a delivery status of a first medical object, the last-known location is provided display responsive to the tracking request.

28 Claims, 7 Drawing Sheets

Related U.S. Application Data continuation of application No. 16/377,088, filed on Apr. 5, 2019, now Pat. No. 11,295,842, which is a continuation of application No. 15/707,975, filed on Sep. 18, 2017, now Pat. No. 10,262,113, which is a continuation of application No. 15/136,147, filed on Apr. 22, 2016, now Pat. No. 9,767,256, which is a continuation of application No. 14/498,915, filed on Sep. 26, 2014, now Pat. No. 9,449,356, which is a continuation of application No. 13/026,953, filed on Feb. 14, 2011, now Pat. No. 8,844,803.

(51) Int. Cl.
| | |
|---|---|
| G16H 20/10 | (2018.01) |
| G16H 20/17 | (2018.01) |
| G16H 40/20 | (2018.01) |
| G16H 40/40 | (2018.01) |
| G16H 40/60 | (2018.01) |
| G16H 70/40 | (2018.01) |

(52) U.S. Cl.
CPC ......... *G06Q 10/0833* (2013.01); *G16H 10/60* (2018.01); *G16H 20/10* (2018.01); *G16H 20/17* (2018.01); *G16H 40/20* (2018.01); *G16H 40/40* (2018.01); *G16H 40/60* (2018.01); *G16H 70/40* (2018.01)

(58) Field of Classification Search
CPC .... G16H 40/60; G16H 70/40; G06K 7/10386; G06K 7/1408; G06Q 10/0833
See application file for complete search history.

(56) References Cited

U.S. PATENT DOCUMENTS

| | | |
|---|---|---|
| 2002/0095238 A1 | 7/2002 | Ahlin et al. |
| 2003/0048187 A1 | 3/2003 | Nolte |
| 2003/0095112 A1 | 5/2003 | Kawano et al. |
| 2004/0008123 A1 | 1/2004 | Carrender et al. |
| 2005/0006470 A1 | 1/2005 | Mrozik et al. |
| 2005/0055242 A1 | 3/2005 | Bello et al. |
| 2005/0234641 A1 | 10/2005 | Marks et al. |
| 2006/0065713 A1 | 3/2006 | Kingery |
| 2006/0122729 A1 | 6/2006 | Murphy et al. |
| 2006/0290519 A1 | 12/2006 | Boate et al. |
| 2007/0233521 A1 | 10/2007 | Wehba et al. |
| 2008/0211674 A1 | 9/2008 | Gibson et al. |
| 2009/0106692 A1 | 4/2009 | Bhavani |
| 2009/0127327 A1 | 5/2009 | Rani |
| 2009/0138122 A1 | 5/2009 | Wagner |
| 2009/0230189 A1 | 9/2009 | Louie et al. |
| 2010/0134257 A1 | 6/2010 | Puleston et al. |
| 2010/0274587 A1 | 10/2010 | Gamboa et al. |
| 2010/0324936 A1 | 12/2010 | Vishnubhatla et al. |
| 2011/0018828 A1 | 1/2011 | Wu et al. |

FOREIGN PATENT DOCUMENTS

| | | |
|---|---|---|
| KR | 100738253 B1 | 7/2007 |
| KR | 1020100018217 | 2/2010 |
| KR | 1020100023326 | 3/2010 |
| KR | 1020100063769 | 6/2010 |

OTHER PUBLICATIONS

European Office Action for Application No. 12746815.5, dated Aug. 8, 2018, 6 pages.

Extended European Search Report for Application No. 12746815.5, dated Jun. 3, 2016, 7 pages.

International Search Report and Written Opinion for Application No. PCT/US2012/024769, dated Sep. 12, 2012, 11 pages.

International Search Report and Written Opinion for Application No. PCT/US2012/056924, dated Mar. 14, 2013, 11 pages.

European Summons to attend oral proceedings pursuant to Rule 115(1) EPC for Application No. 12746815.5, dated Jun. 4, 2019, 13 pages.

400A

410A
- PATIENT: Jane Smith, Jr.
- MEDICATION: bupivicanine IV solution
- DELIVERY LOCATION: Medication Storage (#307)
- DELIVERY PERSON: Kevin Doe
- TRACK REQUEST TIME: 11:03 am
- DELIVERY STATUS: In-transit

420A

| READ | READ LOCATION | TIME |
|---|---|---|
| 1 | Pharmacy Fill/Prep Area (#420) | 9:05 am |
| 2 | Pharmacy Pharmacist (#425) | 9:30 am |
| 3 | Pharmacy Pickup Area (#430) | 10:17 am |
| 4 | Operating Room 1 (#305) | 10:45 am |

410B
- PATIENT: Jane Smith, Jr.
- MEDICATION: bupivicanine IV solution
- DELIVERY LOCATION: Medication Storage (#307)
- DELIVERY PERSON: Kevin Doe
- TRACK REQUEST TIME: 11:15 am
- DELIVERY STATUS: Completed

420B

| READ | READ LOCATION | TIME |
|---|---|---|
| 1 | Pharmacy Fill/Prep Area (#420) | 9:05 am |
| 2 | Pharmacy Pharmacist (#425) | 9:30 am |
| 3 | Pharmacy Pickup Area (#430) | 10:17 am |
| 4 | Operating Room 1 (#305) | 10:45 am |
| 5 | Medication Storage (#307) | 11:10 am |

FIG. 4B

SYSTEM AND METHOD FOR MONITORING PROGRESS OF DELIVERY OF A MEDICAL OBJECT

CROSS-REFERENCE TO RELATED APPLICATIONS

This application is a continuation of application Ser. No. 17/713,193, filed on Apr. 4, 2022, now U.S. Pat. No. 11,763,925, which is a continuation of application Ser. No. 16/377,088, filed on Apr. 5, 2019, now U.S. Pat. No. 11,295,842, which is a continuation of application Ser. No. 15/707,975, filed on Sep. 18, 2017, now U.S. Pat. No. 10,262,113, which is a continuation of application Ser. No. 15/136,147, filed on Apr. 22, 2016, now U.S. Pat. No. 9,767,256, which is a continuation of application Ser. No. 14/498,915, filed on Sep. 26, 2014, now U.S. Pat. No. 9,449,356, which is a continuation of application Ser. No. 13/026,953, filed on Feb. 14, 2011, now U.S. Pat. No. 8,844,803, the entirety of each of which is incorporated herein by reference for all purposes.

FIELD

The present disclosure generally relates to medication distribution, and, in particular, relates to systems and methods for monitoring progress of delivery of a patient-specific medication in a healthcare facility.

DESCRIPTION OF THE RELATED ART

In a healthcare facility, such as a hospital, a pharmacist or pharmacy department within the hospital can coordinate dispensing of medications prescribed to patients (patient-specific medications) within the hospital. In recent years, some hospitals have been assisted with drug distribution management by implementation of automatic dispensing machines (ADMs). ADMs have effectively created branches of the hospital pharmacy department at different nursing stations where the ADMs are located.

It has been reported that the implementation of ADMs have decreased the time to first doses of those medications available in the ADM. However, for those medications not dispensed by the ADM (e.g., medications stored in a locked cabinet or a refrigerator), significant time of a care provider (e.g., nurse) can be spent on attempting to locate a given dose of a patient-specific medication. For example, the non-ADM-dispensed medication may be delivered to a counter, a shelf, or a hanger (e.g., for an IV bag), and the care provider would be unable to track the delivery of the medication.

While some ADMs allow the care provider to track medications that are currently available at the ADM, they do not provide any indication of the progress of delivery of any medications that are currently not available at the ADM. Knowing where the medication is and/or when to expect the medication at the delivery location can enhance operational efficiencies of medication dispensing by allowing the care provider to quickly locate the patient-specific medication and/or more effectively manage his/her time.

SUMMARY

For some or all of the reasons listed above, there is a need for systems and methods that allow a care provider to monitor progress of delivery of a patient-specific medication in a healthcare facility, and to provide trackable locations of medications other than an ADM.

In certain aspects of the present disclosure, a system for monitoring progress of delivery of a medication prescribed to a patient is provided. The medication is to be delivered to a delivery location in a healthcare facility. The system can comprise a patient/medication identification (ID) device provided on a package containing the medication, the patient/medication ID device comprising medication/patient information indicative of the medication and the patient. The system can further comprise at least one location ID device provided at a location, the at least one location ID device comprising a unique location ID associated with the location. The system can further comprise at least one reader device configured to read the medication/patient information from the patient/medication ID device and the unique location ID from the at least one location ID device. The system can further comprise a processor in data communication with the reader device and configured to receive the medication/patient ID information and the unique location ID, and generate delivery progress information indicative of a last-known read location where at least one of the patient/medication ID information and the unique location ID was read by the at least one reader device. The system can further comprise a database in data communication with the processor and configured to store the delivery progress information. The system can further comprise a tracking device in data communication with the database and configured to indicate a progress of the delivery of the medication to the user based on the delivery progress information.

In certain aspects of the present disclosure, a method of monitoring progress of delivery of a medication prescribed to a patient is provided. The medication is to be delivered to a delivery location in a healthcare facility. The method can comprise providing a patient/medication identification (ID) device on a package containing the medication, the patient/medication ID device comprising medication/patient information indicative of the medication and the patient. The method can further comprise providing at least one location ID device at a location, the at least one location ID device comprising a unique location ID associated with the location. The method can further comprise reading the medication/patient information from the patient/medication ID device and the patient/medication ID from the patient/medication ID. The method can further comprise generating delivery progress information indicative of a last-known read location where at least one of the medication/patient ID information and the unique location identifier was read. The method can further comprise storing the delivery progress information in a database. The method can further comprise accessing the delivery progress information from the database in response to the request. The method can further comprise indicating a delivery status of the medication to the user.

In certain aspects of the present disclosure, a system for monitoring progress of delivery of a medication prescribed to a patient is provided. The medication is to be delivered to a delivery location in a healthcare facility. The system can comprise a patient/medication identification (ID) device provided on a package containing the medication, the patient/medication ID device comprising medication/patient information indicative of the medication and the patient. The system can further comprise a plurality of reader devices provided at a plurality of read locations and configured to read the medication/patient information from the patient/medication ID device. The system can further comprise a processor in data communication with the reader devices and configured to receive the medication/patient ID information read by a particular reader device among the plurality of reader devices and location information indicative of the particular reader device or a corresponding read location of the particular reader device, and generate delivery progress information indicative of a last-known read location where the medication/patient ID information was read by the particular reader device based on the medication/patient ID information and the location information. The system can further comprise a database in data communication with the processor and configured to store the delivery progress information. The system can further comprise a tracking device in data communication with the database and configured to receive a tracking request by a user, access the delivery progress information from the database in response to the request, and indicate a delivery status to the user based on the delivery progress information.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments.

FIGS. 4A and 4B depict exemplary displays that provides delivery progress indications in response to a tracking request made at a first time and a second time, respectively, according to certain aspects of the present disclosure.

DETAILED DESCRIPTION

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Figure 1:
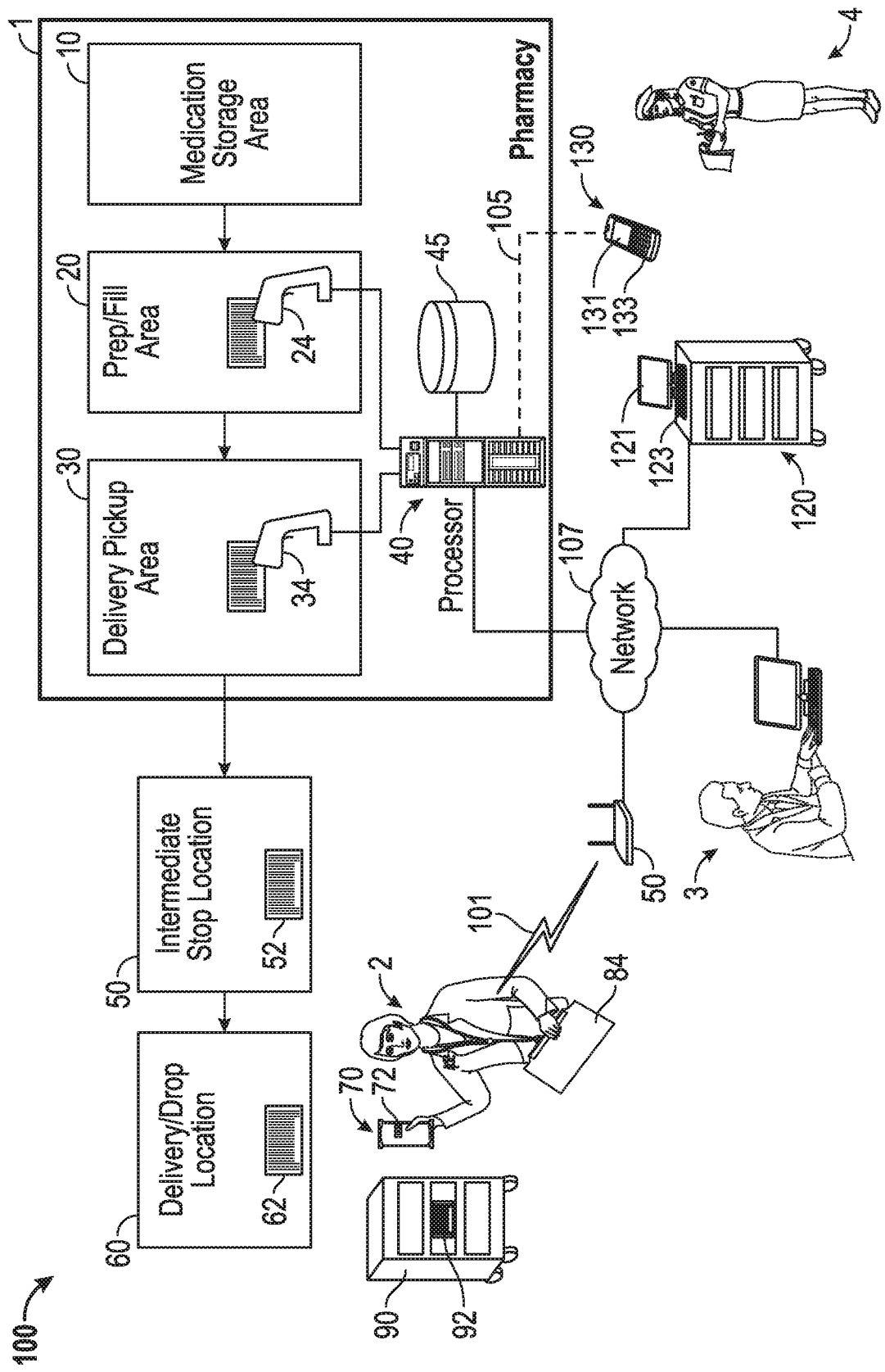
FIG. 1 is a diagram depicting an exemplary system for monitoring delivery of a patient-specific medication in a healthcare facility according to certain aspects of the present disclosure.

FIG. 1 is a diagram depicting an exemplary system 100 for monitoring delivery of a patient-specific medication in a healthcare facility according to certain aspects of the present disclosure. For ease and clarity of illustration only, without any intent to limit the scope of the present disclosure any way, it is assumed that the patient-specific medication is an epidural anesthetics IV solution that can be used during a child delivery, for example.

The system 100 includes a pharmacy 1 having a medication storage area 10, a fill and/or preparation (fill/prep) area 20, and a delivery pickup area 30. The medication storage area 10 includes a plurality of medications and supplies including an anesthetic drug (e.g., bupivicanine or chloroprocaine) and an appropriate fluid for the anesthetic drug. The anesthetic drug and the fluid are taken from the medication storage area 10 to the prep/fill area 20 where they are mixed together to produce the epidural anesthetics IV solution. A patient/medication ID device 72, such as a barcode label or an RFID tag, is provided on (e.g., affixed to) a package 70 (e.g., IV bag) containing the IV solution at the prep/fill area 20. The patient/medication ID device 72 includes patient/medication ID information indicative of the medication and the patient to whom the medication is prescribed. The package 70 is then taken by a technician at the pharmacy 1 to the delivery pickup area 30 where it is loaded onto a delivery cart 90 for delivery to a scheduled delivery/drop location 60 ("Medication Storage #307") by a delivery person 2.

In the illustrated embodiment, the prep/fill area 20 has a barcode reader 24 provided therein that the technician at the pharmacy 1 can use to read the patient/medication ID device 72 (a barcode label in the illustrated example) before the package 70 is taken to the delivery pickup area 30. The delivery pickup area 30 has a barcode reader 34 provided therein that the technician at the pharmacy 1 can use to read the patient/medication ID device 72 once the package 70 is taken to the delivery pickup area 30. The delivery cart 90 may also be provided with a location barcode label 92. The pharmacy 1 also includes a processor (e.g., pharmacy server) that is configured to receive an order for the patient-specific medication from a doctor 3. The processor 40 is coupled to a medication database 45 that is configured to store a variety of information including order status information and delivery progress information to be discussed below.

Also depicted in FIG. 1 is an intermediate stop location 50 ("Operating Room 1 #305"), located between the pharmacy 1 and the delivery location 50, where the delivery cart makes a temporary stop, e.g., for delivering another package containing a medication for another patient.

The delivery location 60 and/or the intermediate stop location 50 can include, for example, a cabinet or a refrigerator for storing a patient-specific medication before use. In the illustrated example, the intermediate stop location 50 and the delivery location 60 are provided with location barcode label 52 and location barcode label 62, respectively. Each of the location barcode labels 52, 62 includes a unique location ID information indicative of the respective location 50, 60 where the corresponding barcode label is provided. As described above, the package 70 (e.g., IV bag) containing the patient-specific medication (e.g., IV solution) is provided with a patient/medication identification (ID) device 72. In the illustrated example, the patient/medication ID device 72 is a barcode label that includes patient/medication information indicative of the patient (e.g., "Jane Smith") and the medication (e.g., "bupivicanine IV solution"). The patient/medication information may also contain other drug or patient related information such as the patient's medical conditions (e.g., allergies), name of the drug (e.g., bupivicanine), the drug dosage, the drug concentration, the drug administration schedules, and the drug delivery rate.

Also depicted in the system 100 of FIG. 1 is a reader device 84 that is hand carried by the delivery person 2 and/or attached to the delivery cart 90 and is configured to read the patient/medication information from the patient/medication ID device 72 provided on the package 70. In the illustrated example, the reader device 84 is a barcode scanner. In those embodiments in which the barcode scanner 84 is hand carried by the delivery person 2, the scanner 84 is also configured to read the location ID information from the location barcode labels 52, 62, 92.

In the embodiments described above, the location ID devices 52, 62, 92 and/or the patient/medication ID device 72 are passive ID devices, meaning that certain action (e.g., scanning) has be taken by the participant (e.g., a pharmacy technician or the delivery person 2) to retrieve information therefrom. In other embodiments, the ID devices can be active ID devices, meaning that the information retrieval from the ID devices occur automatically without an action taken by the participant. In some embodiments, the active ID devices can actively transmit signals containing the relevant information to the reader device 72 through a wireless link. The wireless link can use a variety of technologies including Bluetooth, ZigBee, wireless USB, and proprietary systems. In other embodiments, the active ID devices do not themselves transmit signals, but respond to query signals generated by a reader device (e.g., by altering impedance of an RF circuit therein) as the reader device passes by the ID devices in close proximity.

In the illustrated example, each time the barcode scanner 84 scans an ID device (e.g., patient/medication ID device or location ID device), the information read thereby is wirelessly transmitted over a mobile device link 101 to a wireless bridge 50 that receives the information. The bridge 50 is in data communication with the processor 40 via a hospital network 107.

The processor 40 is configured to receive medication/patient ID information and/or location ID information read by the barcode scanner 84, generate delivery progress information therefrom, and store the delivery progress information in the medication database 45. The delivery progress information can include, but is not limited to: the patient's name or ID; the medication name or ID, the scheduled delivery location 60, one or more read locations where the medication/patient ID information and/or the location ID information was read by the barcode scanner 84, time when the information was read, and the name or ID of the delivery person 2.

The system 100 further comprises tracking devices 120, 130 that allow a care provider 4 (e.g., a nurse assigned the task of administering the patient-specific medication to the patient) to monitor the progress of the delivery of the medication. Each of the tracking devices 120, 130 is configured to receive a tracking request by the care provider 4, access the medication database 45, either directly or via the processor 40, retrieve the delivery progress information stored in the database 45, and indicate a delivery progress of the medication to the care provider 4 based on the delivery progress information. In the illustrated example, the tracking device 120 is an ADM having a processor (not shown), a display 121, and a keyboard 123; and the tracking device 130 is a mobile communication device (e.g., a cell phone, personal digital assistant (PDA), or pager) having a processor (not shown), a display 131, and a keyboard 133. The delivery progress information can inform the care provider 4 of a last-known read location and time of the last reading. Based on such information, the care provider 4 can decide, e.g., whether to wait for the delivery at the delivery location 60, go to the delivery location later at an expected delivery time, or go to the last-known location to retrieve the medication from the cart 90.

Figure 2A:
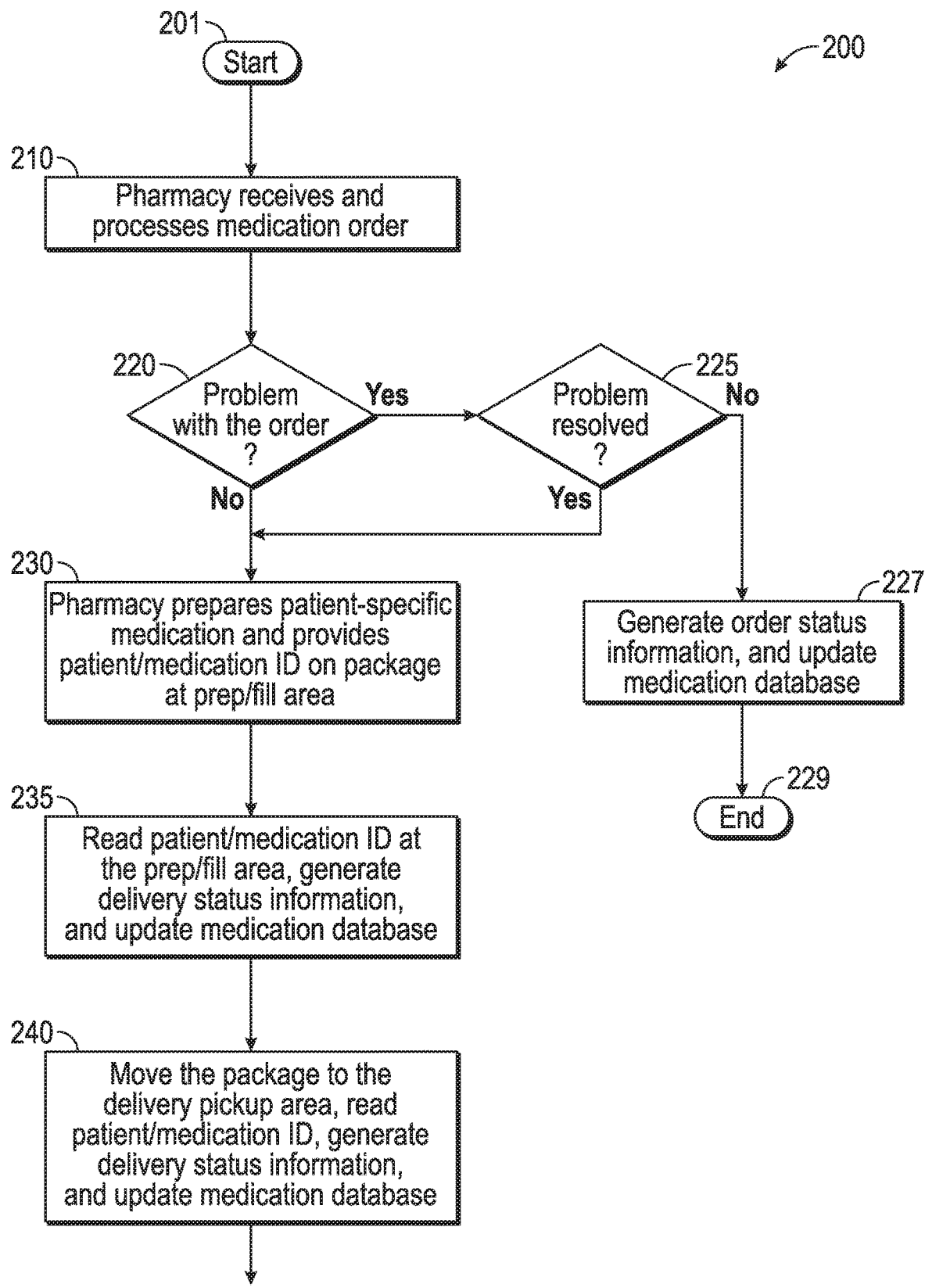
FIGS. 2A and 2B show a flowchart illustrating an exemplary process for monitoring delivery of a patient-specific medication according to certain aspects of the present disclosure.
Figure 2B:
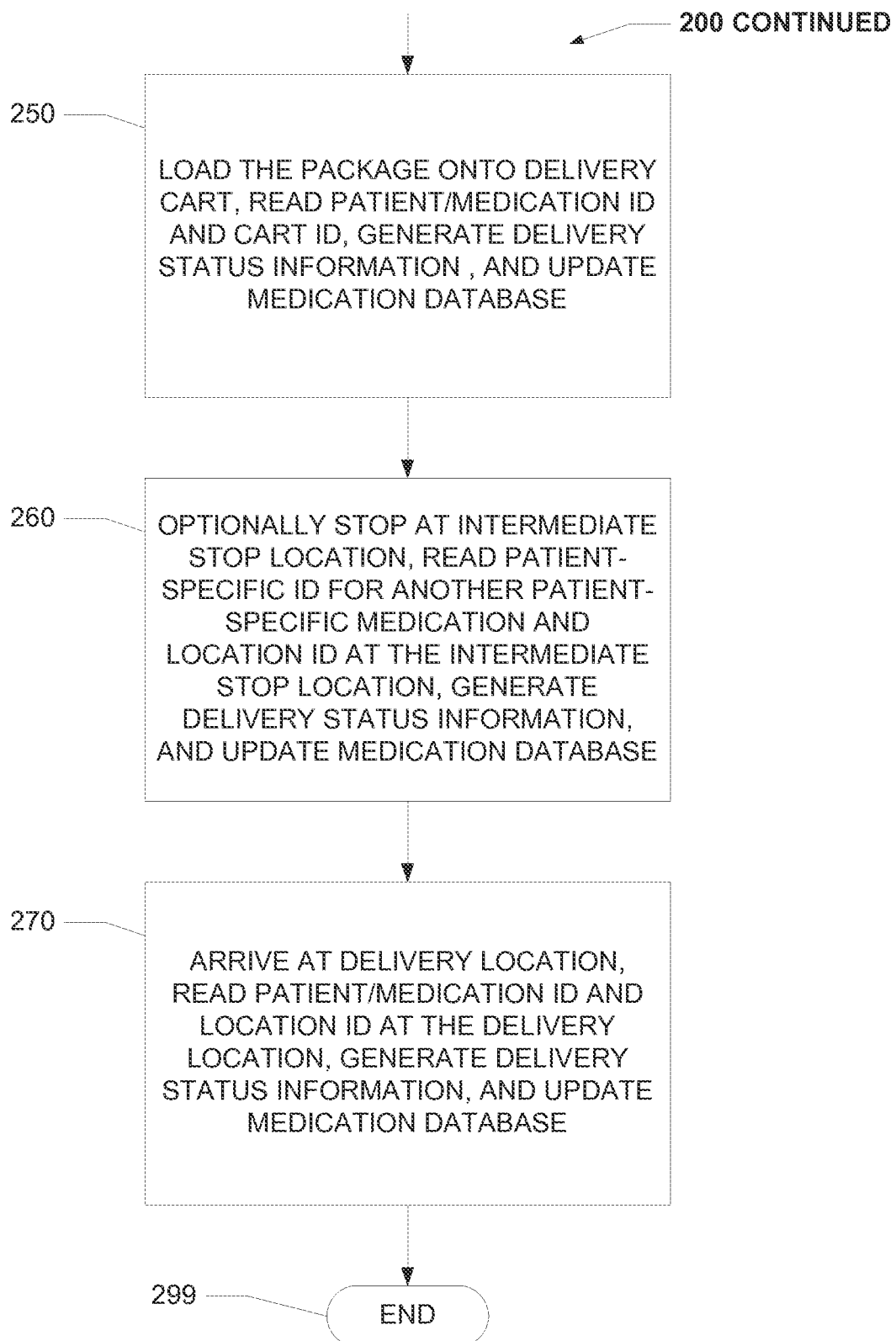

FIGS. 2A and 2B show a flowchart (FIG. 2B continued from FIG. 2A) illustrating an exemplary process 200 for monitoring delivery of a patient-specific medication according to certain aspects of the present disclosure. For ease of illustration, without any intent to limit the scope of the present disclosure in any way, the process 200 will be described with reference to the system 100 of FIG. 1. A person skilled in the art shall appreciate that the process 200 can be implemented in a system that is different from the system 100 without departing from the scope of the present disclosure. As an initial matter, it is hereby assumed that all location ID devices (e.g., location barcode labels 52, 62, 92) are provided on respective locations/areas 50, 60, 90.

The process 200 begins at start state 201 and proceeds to operation 210 in which pharmacy 1 (e.g., by the processor 40 and/or a pharmacist) receives and processes a medication order from the doctor 3. The process 200 proceeds to decision state 220 in which it is determined (e.g., by the processor 40 and/or the pharmacist) whether there is a problem with the medication order. Non-limiting examples of such a problem can include: the pharmacy 1 currently being out of stock of the patient-specific medication or an ingredient (drug or fluid) needed for preparing the medication; and the medication or an aspect thereof (e.g., delivery dosage) not complying with an established rule for the medication and/or the patient.

If the answer to the determination at the decision state 220 is Yes (a problem encountered with the medication order), the process 200 proceeds to another decision state 225 where it is determined whether the problem has been resolved or reconciled. If the answer is No, the process 200 proceeds to operation 227 in which an order status information indicating the problem encountered with the medication order (e.g., "Out of Stock") is generated, and the medication database 45 is updated accordingly, and the process 200 ends at end state 229.

On the other hand, if the answer to the determination at the decision state 220 or at the decision state 225 is No (no problem with the medication order or the problem has been resolved), the process 200 proceeds to operation 230 in which the pharmacy 1 prepares the patient-specific medication. In the assumed example of the IV solution, the preparation can include taking a drug (e.g., bupivicanine) and a fluid (e.g., a saline solution) from the medication storage area 10 to the prep/fill area 20, preparing an IV solution comprising the drug and the fluid, and filling a package (an IV bag) with the IV solution. After the preparing and filling, a patient/medication ID device (e.g., a barcode label 72) is provided on the package 70 at the prep/fill area 20.

The process 200 proceeds to operation 235 in which the patient/medication information in the barcode label 72 is read by the barcode scanner 24 at the pharmacy prep/fill area 20 and sent to the processor 40. The processor 40 generates delivery progress information from the patient/medication information received from the barcode scanner 24, and updates (e.g., stores) the medication database 45 with the delivery progress information. If the care provider 4 were to make a medication track request after this point (but before the package 70 is delivered to the delivery pickup area 30 (operation 240)), the tracking device 120, 130 would indicate the prep/fill area 20 as the last-known read location.

The process 200 proceeds to operation 240 in which the package 70 containing the patient-specific medication is moved to the deliver pickup area 30. At the delivery pickup area 30, the patient/medication information in the barcode label 72 is read by the barcode scanner 34 and sent to the processor 40. The processor 40 generates new delivery progress information from the patient/medication received from the barcode scanner 34, and updates (e.g., stores) the medication database 45 with the new delivery progress information. If the care provider 4 were to make a medication track request after this point (but before the package 70 is loaded onto the delivery cart 90 (operation 250)), the tracking device 120, 130 would indicate the delivery pickup area 30 as the last-known read location for the package Additionally, an optional location barcode label may be provided in the delivery pickup area 30 that can be read by the barcode scanner 34 or an optional handheld barcode scanner located in the delivery pickup area 30 to furnish the location information of the package 70.

In certain embodiments, before the package 70 containing the patient-specific medication is moved to the delivery pick-up area 30, a pharmacist at a pharmacist location in the pharmacy 1 performs a check of the content of the package 70 to ensure that the package contains the right medication.

The process 200 proceeds to operation 250 in which the package 70 containing the patient-specific medication is loaded onto the delivery cart 90 by, e.g., the delivery person 2. The patient/medication information in the barcode label 72 of the package 70 and the location ID information in the barcode label 92 are read by the barcode scanner 84 carried by the delivery person 2 and sent to the processor 40. The processor 40 generates new delivery progress information from the patient/medication received and the location ID information from the barcode scanner 84, and updates (e.g., stores) the medication database 45 with the new delivery progress information. If the care provider 4 were to make a medication track request after this point, the tracking device 120, 130 would indicate the delivery cart 90 as the last-known read location.

The process 200 proceeds to operation 260 in which the delivery cart 90 carrying the package 70 arrives at the intermediate stop location 50, e.g., for delivering another package containing another patient-specific medication for a different patient. In that case, other patient/medication information associated with the other patient-specific medication and the location information in the location barcode label 52 provided at the location 50 are read by the barcode scanner 84 and sent to the processor 40 to indicate the delivery of the other package at the intermediate stop location 50. The processor 40 generates delivery progress information for the other patient-specific medication from the other patient/medication information and the location information received from the barcode scanner 84, and updates (e.g., stores) the medication database 45 with the delivery progress information for the other patient-specific medication. In some embodiments, the system 1 can also track the location of the cart 90 containing the package 70 by using the delivery information for the other patient-specific medication even though the package 70 is not delivered to the intermediate stop location 50. By tracking the intermediate stop location(s) of the cart 90, the system 1 can provide more updated current location(s) of the patient-specific medication. For example, if the care provider 4 were to make a medication track request after this point (but before the cart 90 arrives at the delivery location 60 (operation 270)), the tracking device 120, 130 would indicate the intermediate stop location 50 as the last-known location of the cart 90 carrying the package 70 (and hence the patient-specific medication). However, the cart 90 is a mobile location. The scheduled delivery location 60 is considered a "stationary" location. Tracking items on a delivery cart is more readily achievable than once the items have been delivered to a stationary location using conventional technology. This may be due to the relative control that a caregiver has over items being transported though a hospital or other health care facility. By comparison, once the item is removed from the mobile cart and provided at a stationary location, there has not been a tracking of that item at that stationary location. There is no record therefore, of the item location once removed from the mobile cart. The embodiments of the present disclosure address such concerns regarding stationary locations.

The process 200 proceeds to operation 270 in which the delivery cart 90 carrying the package 70 arrives at the scheduled delivery location 60. At the delivery location 60, the patient/medication information in the barcode label 72 and the location information in the location barcode label 62 are read by the barcode scanner 84 and sent to the processor 40. The computer 40 generates new delivery progress information from the patient/medication and location information received from the barcode scanner 84, and updates (e.g., stores) the medication database 45 with the new delivery progress information. If the care provider 4 were to make a medication track request after this point, the tracking device 120, 130 would indicate the delivery location 60 as the last-known read location. The process 200 ends at state 299.

Figure 3:
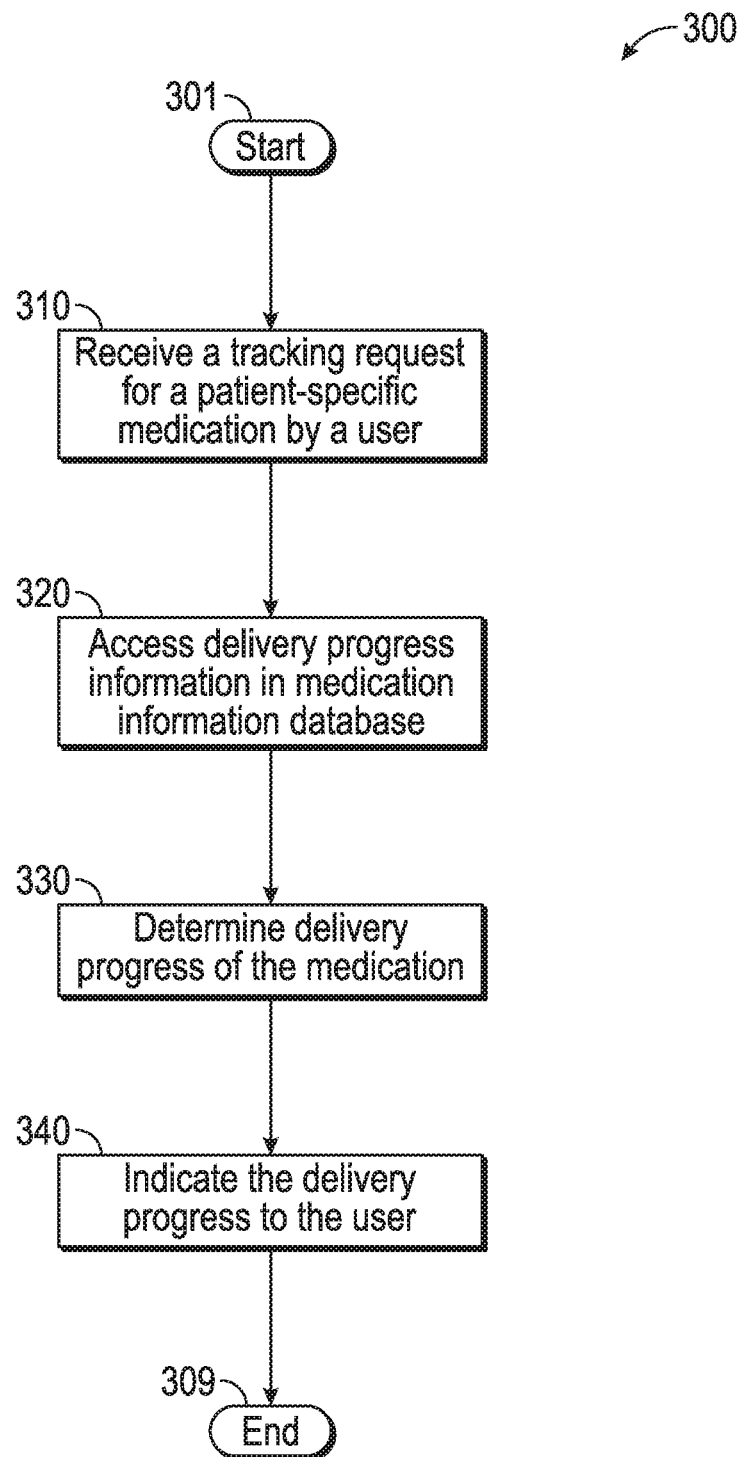
FIG. 3 is a flowchart illustrating an exemplary process for monitoring delivery of a patient-specific medication from the perspective of a tracking device according to certain aspects of the present disclosure.

FIG. 3 is a flowchart illustrating an exemplary process 300 for monitoring delivery of a patient-specific medication from the perspective of a tracking device (e.g., 120, 130) according to certain aspects of the present disclosure. As with the process 200 of FIG. 2, for the ease of illustration, the process 300 will be described with reference to the system 100 of FIG. 1. A person skilled in the art shall appreciate that the process 300 can be implemented in a system that is different from the system 100 without departing from the scope of the present disclosure.

The process 300 begins at start state 301 and proceeds to operation 310 in which a tracking request for the patient-specific medication is received by the tracking device 120, 130 from the care provider 4. Assuming that the tracking device from which the tracking request is made is the ADM 120 shown in FIG. 1, the tracking request can be made by the care provider 4 entering request data, such as the patient's name and/or a medication order number, using the keyboard 123 of the ADM 120.

The process 300 proceeds to operation 320 in which, after receiving the tracking request, the tracking device 120, 130 accesses the medication database 45 and retrieves the delivery progress information stored therein. In certain embodiments, the database 45 is accessed directly by the tracking device 120, 130. In other embodiments, the database 45 is accessed via the processor 40. In some embodiments, the tracking device 120, 130 retrieves the order status information in addition to the delivery progress information. For example, when the tracking device 120, 130 determines that the delivery progress information indicates that the patient-specific medication has not been prepared and filled (e.g., by lack of an ID reading at the prep/fill area 20), the tracking device 120, 130 can retrieve the order status information also stored in the database 45 to determine whether there is any problem with the medication order.

The process 300 proceeds to operation 330 in which the tracking device 120, 130, upon retrieving the delivery progress information, determines, based on the retrieved information, a delivery progress of the patient-specific medication. The delivery progress can include, but is not limited to, the last-known read location where the patient/medication ID device 72 and/or a location ID device 52, 62, 92 was read, time of the reading, and a delivery status (e.g., whether the patient-specific medication has been delivered to the scheduled delivery location 60).

The process 300 proceeds to operation 340 in which the delivery progress so determined is indicated to the care provider 4 who made the medication tracking request. In those embodiments in which the tracking device 120, 130 also retrieves the order status information from the medication database 45, a problem, if any, that was encountered with the medication order can also be indicated. In certain embodiments, the delivery progress and/or the order status can be displayed on the display 121, 131 of the respective tracking device 120, 130. In those embodiments in which delivery information associated with another package may be used for tracking the cart 90 as described above with respect to the operation 260, the last-known cart location may also be indicated. Examples of such a display of the delivery progress information are provided in FIGS. 4A and 4B. After completion of operation 340, the process 300 proceed to an end state 309.

For instance, FIG. 4A depicts an exemplary display 400A that provides a delivery progress indication in response to a tracking request made at a first time (11:03 am). The display 400A includes a header section 410A that indicates the patient ("Jane Smith"), the medication ("bupivicanine IV solution"), the delivery location ("Medication Storage (#307)"), the delivery person ("Kevin Doe"), the tracking request time (11:03 am), and the delivery status ("In-transit"). The display 400A also includes a read list 420A that indicates read locations where readings of the patient/medication ID and/or the location ID were made by the reader device 84, 24, 34, and times of the readings. The list 420A indicates that the last-known read location is Operating Room 1 (#305), corresponding to the intermediate stop location 50 (FIG. 1).

FIG. 4B depicts an exemplary display 400B that provides a delivery progress indication in response to a tracking request made at a second time (11:15 am). The display 400B includes header 410B and read list 420B. The header list 410B indicates that the latest tracking request was made at 11:15 am and that the delivery status is indicated as "Completed" reflecting the fact that the package 70 was delivered to the delivery location 60 at 11:10 am, as indicated in the read list 420B.

Figure 5:
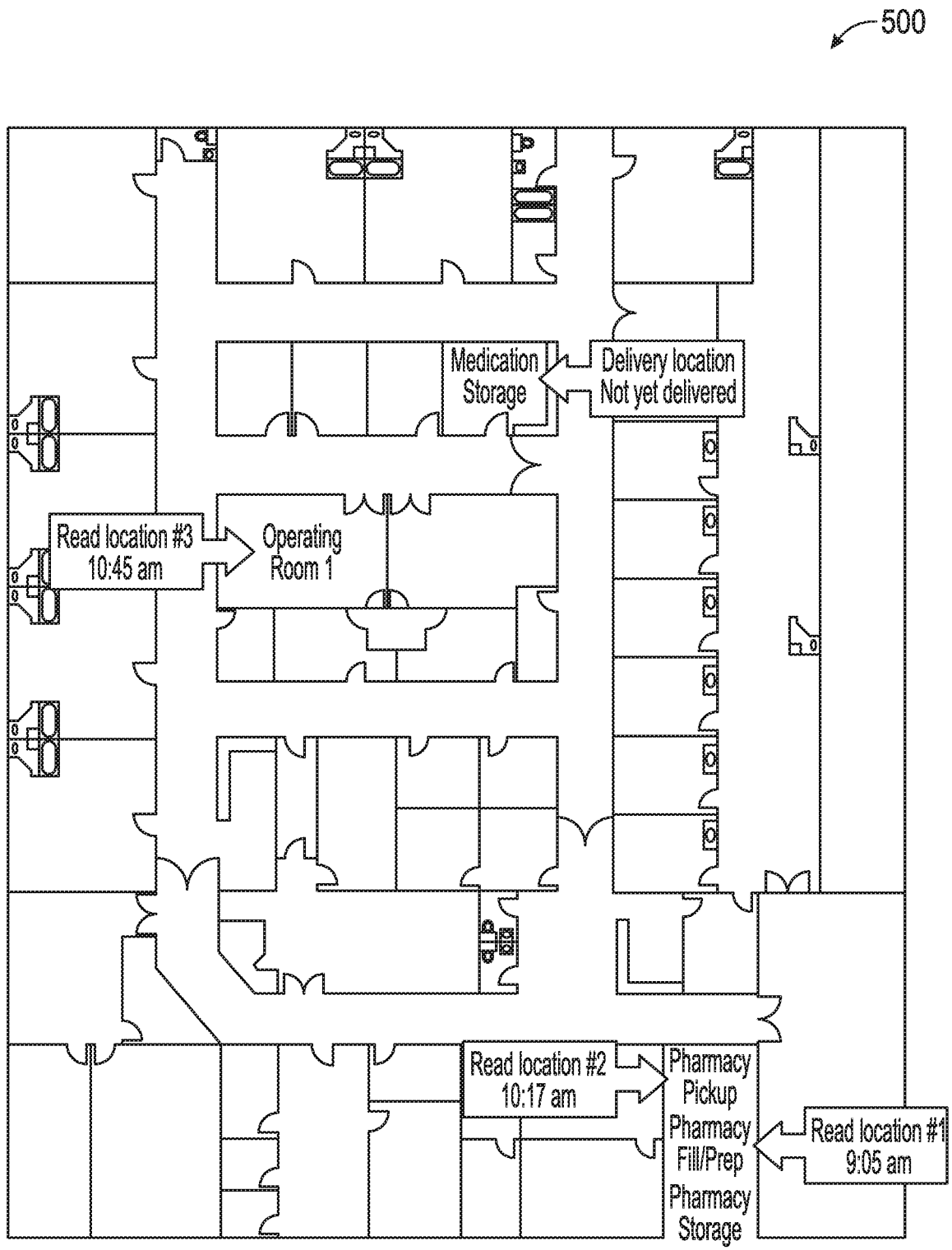
FIG. 5 depicts an exemplary display of a hospital map with read locations as of the first time with corresponding read locations indicated thereon.

In some embodiments, in lieu of or in addition to presenting the read locations in such a text format as in FIGS. 4A and 4B, the read locations can be indicated (e.g., juxtaposed) on a map of the healthcare facility. FIG. 5 depicts an exemplary display 500 of a hospital map with read locations with corresponding read locations indicated thereon as of the first time (11:03 am).

In certain embodiments, the system 100 allows the care provider 4 to receive an electronic message when the package 70 is delivered to the delivery location 60. For example, the processor 40 can be configured to send, upon determining the delivery, a phone-, e-mail-, and/or pager-message to the mobile communication device 130 carried by the care provider 4. By way of example, a monitoring software running on the processor 40 can be programmed such that when the location ID information received from the reader device 84 indicates that the last-known read location corresponds to the scheduled delivery location 60, the software causes the processor 40 to automatically send an electronic message to the mobile communication device 130 via the network 107, an Internet, or a cellular network. In some embodiments, the processor 40 is configured to send an electronic notification when a medication order is not filled within a predetermined time (e.g., 2 hours) after the pharmacy 1 receives the order. Such automatic notification features further provide further operational efficiencies by eliminating the need for the care provider 4 to repeatedly check for the medication fill and/or delivery status.

In certain embodiments, various aspects of the present disclosure can be utilized to implement an inventory control system in an acute care facility that tracks a patient-specific medication through a supply chain (e.g., from a pharmacy to a delivery location). In such a system, information (e.g., medication/patient information and location IDs) can be collected from various locations in the acute care facility and stored in real time in a database with a web/agent front end. The web/agent can aggregate the information in context of a patient's needs. A caregiver (e.g., a nurse) in the acute care facility assigned to the patient can be automatically notified of an availability status of the patient-specific medication. For instance, the caregiver can receive a notification when the medication has become unavailable or about to be stocked out in the pharmacy or in a medication dispensing device (e.g., ADM). The caregiver can also be notified of a status of orders pertaining to the caregiver's patients such as when the orders are in queue, what the length of the queue is, and/or if the orders are cleared. The automatic notification can be received through cell phone text messaging, e-mail messages, or Windows live alerts, for example. Alternatively or additionally, a medication storage device (e.g., ADM) that is configured to store the patient-specific medication can receive and display an automatic notification such as what orders are ready in the queue or what items will be stocked and how soon. Through such automatic notification features, the caregiver can receive timely notification of medication availability in the context of the patient's need. An inventory control system with such features avoids the need for the caregiver to call a pharmacy to check the status of the medication and delays and inefficiencies associated with such checking.

It shall be appreciated that various embodiments of the present disclosure described above are exemplary only and many changes including additions, deletions, and modifications may be made to the embodiments without departing from the scope of the present disclosure. For example, all or some of the read locations 50, 60 and the cart 90 may be provided with respective barcode scanners that are attached to a fixed device (e.g., a computer or a storage cabinet) at the locations. In such embodiments, there is no need to provide for and scan the location barcodes 52, 62, 92 since the respective fixed barcode scanner would "know" where it is located. The patient/medication ID device 72 and/or the location ID devices 52, 62, 92 may be RFID tags instead of the barcode labels, and the reader device 24, 34, 84 may be an RFID reader. The medication database 45 comprising the delivery progress information may reside inside the processor 40 (e.g., pharmacy server). The delivery progress information may be stored in a database that is located outside the pharmacy 1. The package 70 may be hand-carried by the delivery person 4 to the delivery location 60 instead of being carried on the delivery cart 90. The delivery location 60 may be another ADM. The patient-specific medication may already be stored in a pre-labeled container in the pharmacy medication storage area 10 and may not need to be separately prepared and filled at the prep/fill area 20. There may be multiple intermediate stop locations or no intermediate stop location between the pharmacy 1 and the delivery location 60.

Figure 6:
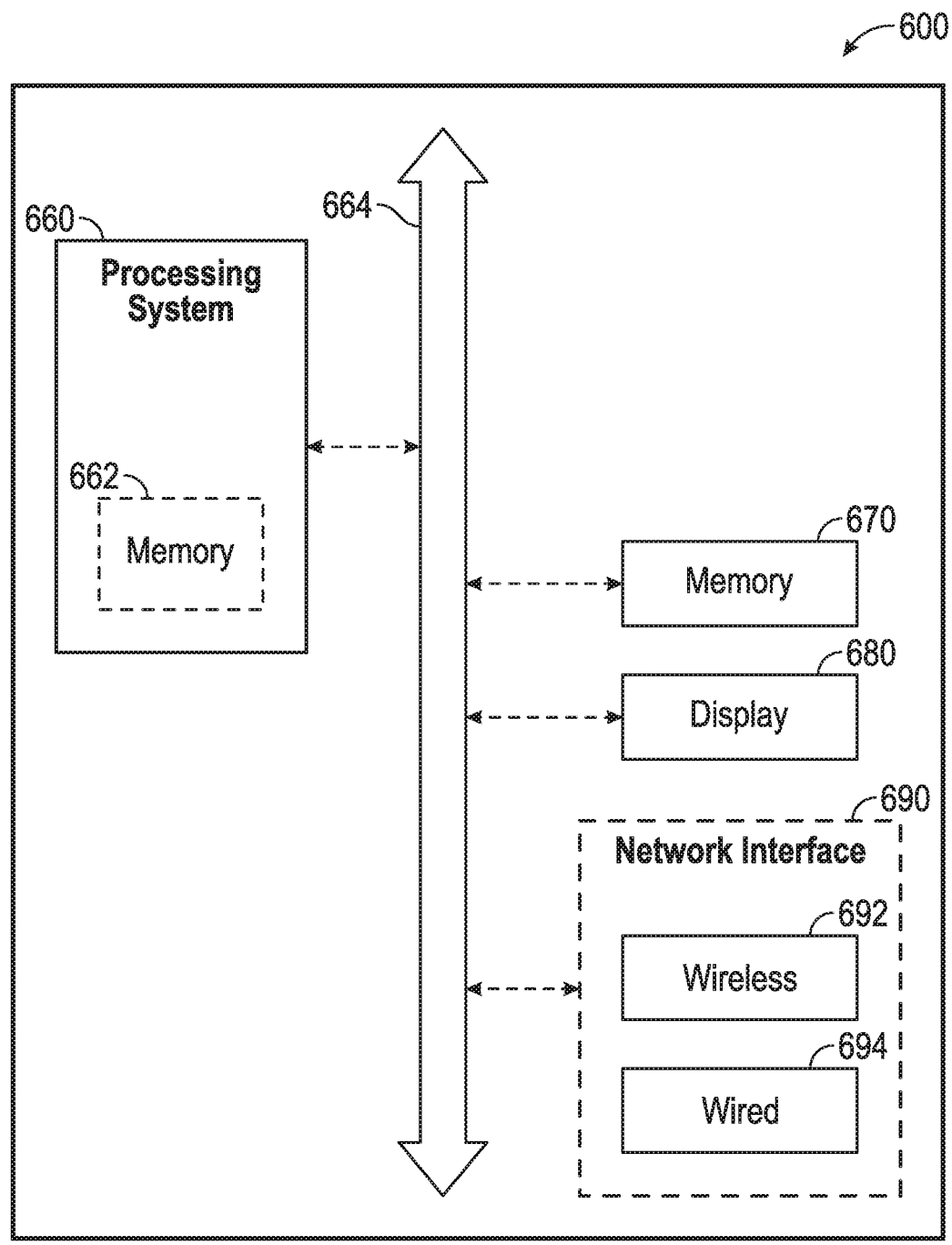
FIG. 6 is a schematic block diagram depicting a computing system that may be employed as the processor depicted in FIG. 1.

FIG. 6 is a schematic block diagram depicting a computing system 600 that may be employed as the processor 40 of FIG. 1. The computing system 600 may be a standard computer server connected to the hospital communication network 107 and located in the pharmacy 1 as shown in FIG. 1 or in a hospital data center or computer room outside the pharmacy 1, although other locations may be employed.

The computing system 600 includes a processor 660, memory 670, display 680, and network interface 690 having a wireless interface 692 and a wired interface 694. The processor 660 may include a general-purpose processor or a specific-purpose processor for executing instructions and may further include a memory 662, such as a volatile or non-volatile memory, for storing data and/or instructions for software programs. The instructions, which may be stored in memories 662 or 670, may be executed by the processor 660 to control and manage the wireless and wired network interfaces 692, 694 as well as provide other communication and processing functions.

The processor 660 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Information such as patient/medication information, medication orders, and possible read locations within the healthcare facility may be stored in memory 662 internal to processor 660, memory 670 external to processor 660, a database external to the computer 600 (e.g., database 45), or any other suitable storage device. The memory 670 or the database 45 may include a Random Access Memory (RAM), flash memory, Read Only Memory (ROM), Programmable Read Only Memory (PROM), Erasable Programmable Read Only Memory (EPROM), registers, a hard disk, a removable disk, a Solid State Memory (SSD).

Memory 662 or 670 can also include the medication database 45 for storing the medication progress information described above with respect to FIGS. 1, 2A-B, and 3. The memory 670 external to the processor 660 or alternatively, the memory 662 internal to the processor 660 may include such an medication database.

Certain aspects of delivery monitoring systems and methods described herein can be performed by the processor 660 executing one or more sequences of one or more instructions contained in an internal machine-readable medium such as the internal memory 662 or the memory 670. For example, the processor 660 can receive the patient/medication information and the location information from the reader device 24, 34, 84 via the network interface 690, generate the delivery progress information based on the received information, and store and retrieve the delivery progress information to and from the medication database 45.

The processor 660 may also send messages to the mobile communication device 130, such as cell phones, PDAs, and pagers, over a mobile device link 105 via the wireless network interface 692 to send an automatic electronic notification when the delivery is completed. The mobile device link 105 may include the hospital network 107 and internal or external wireless communication systems that are capable of sending messages that can be received by mobile device 130.

Such instructions and/or information may be read into the memory 662, 670 from another machine-readable medium, such as a CD, flash memory, or a wireless transmission. Execution of the sequences of instructions contained in the memory 662 causes the processor 660 perform the process steps described herein. One or more processors in a multi-processing arrangement may also be employed to execute the sequences of instructions contained in memory 662. In alternative embodiments, hard-wired circuitry may be used in place of or in combination with software instructions to implement various embodiments. Thus, embodiments are not limited to any specific combination of hardware circuitry and software.

The term "machine-readable medium" as used herein refers to any medium that participates in providing instructions to processor 660 for execution or storing results of or parameters (e.g., variables or constants) for computations such as for the determination of the last-known read locations and whether to send an automatic electronic notification. Such a medium may take many forms, including, but not limited to, non-volatile media, volatile media, and transmission media. Non-volatile media include, for example, optical or magnetic disks, such as data storage device. Volatile media include dynamic memory, such as the memory 670. Transmission media include coaxial cables, copper wire, and fiber optics, including the wires that comprise bus 664. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, a carrier wave, or any other medium from which a computer can read.

Various embodiments of the present disclosure provide a number of advantages over conventional medication dispensing and tracking systems including expanding trackable locations of medications in a healthcare facility. The trackable locations can include the final delivery location of a patient-specific medication and intermediate stop mobile location(s) of delivery means (e.g., cart, tray, person) for carrying the medication. The delivery tracking can be effectuated even if the patient-specific medication is a non-ADM-dispensed medication such as an IV solution.

The foregoing description is provided to enable any person skilled in the art to practice the various embodiments described herein. While the foregoing embodiments have been particularly described with reference to the various figures and embodiments, it should be understood that these are for illustration purposes only and should not be taken as limiting the scope of the claims.

The word "exemplary" is used herein to mean "serving as an example or illustration." Any aspect or design described herein as "exemplary" is not necessarily to be construed as preferred or advantageous over other aspects or designs.

A reference to an element in the singular is not intended to mean "one and only one" unless specifically stated, but rather "one or more." The term "some" refers to one or more. Underlined and/or italicized headings and subheadings are used for convenience only, do not limit the invention, and are not referred to in connection with the interpretation of the description of the invention. All structural and functional equivalents to the elements of the various embodiments of the invention described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. A dispensing device comprising:
a lockable storage configured to store medical items;
a tracking interface comprising a display device; and
a processor,
wherein the dispensing device is configured to:
receive, via the tracking interface, a tracking request for a delivery status of a first medical object;
identify medical identification information that was read at a first location when a medical package associated with the first medical object was read at the first location by a reader device;
identify first location information associated with the first location and the medical package based on the tracking request;
generate, responsive to receiving the tracking request and identifying the first location information, a last-known location of the first medical object based on the first location information;
associate the last-known location and the first medical object in a database; and
provide the last-known location for display at the display device responsive to the tracking request.

2. The dispensing device of claim 1, wherein the first medical object is a medication, and the database is configured to store order status information and an identifier associated with the medication, and
wherein the tracking request includes at least a patient's name and the identifier.

3. The dispensing device of claim 1, wherein the dispensing device is further configured to, when the last-known location of the first medical object corresponds to a delivery location of the first medical object:
determine whether the first medical object is delivered to the delivery location within a time of a predetermined time interval, and store the last-known location as the delivery location and a time that the first medical object was delivered to the delivery location in the database.

4. The dispensing device of claim 1, wherein the dispensing device being configured to identify medical identification information comprises the dispensing device being configured to:
receive a first indication that the medical identification information was read at the first location when the medical package associated with the first medical object was read at the first location by the reader device, the reader device being configured to wirelessly read the medical identification information from the medical package when the medical package is within a range of the reader device.

5. The dispensing device of claim 1, wherein the dispensing device being configured to identify medical identification information comprises the dispensing device being configured to:
provide delivery progress information comprising a delivery time and an identification of a delivery person associated with delivering the first medical object to the last-known location.

6. The dispensing device of claim 1, wherein the dispensing device being configured to provide the last-known location for display at the display device comprises the dispensing device being configured to:
provide an interface identifying the first medical object and listing read locations associated with the first medical object, each read location being presented with a time at which the first medical object was read at the read location.

7. The dispensing device of claim 6, wherein the interface listing the read locations associated with the first medical object comprises:
presenting each read location juxtaposed on a map of a healthcare facility, each read location identifying on the map where the first medical object was read.

8. The dispensing device of claim 6, wherein the dispensing device is further configured to:
provide the interface and the last-known location to a mobile device.

9. The dispensing device of claim 1, wherein the dispensing device being configured to provide the last-known location for display at the display device comprises the dispensing device being configured to:
provide the last-known location for display together with an identification of a patient to which the first medical object is assigned.

10. The dispensing device of claim 1, wherein the dispensing device is further configured to:
determine, based on receiving the medical identification information and the first location information, that the first medical object is on a mobile carrier with a second medical object;
receive, after determining that the first medical object is on the mobile carrier, an indication that the second medical object was delivered to a second location prior to a delivery of the first medical object to a delivery location of the first medical object; and
determine, based on receiving the indication, that the second location is the last-known location of the first medical object.

11. A method comprising:
receiving, via a tracking interface of a dispending device, a tracking request for a delivery status of a first medical object, the tracking interface comprising a display device, and the dispensing device comprising a lockable storage configured to store medical items;
identifying medical identification information that was read at a first location when a medical package associated with the first medical object was read at the first location by a reader device;
identifying first location information associated with the first location and the medical package based on the tracking request;
generating, responsive to receiving the tracking request and identifying the first location information, a last-known location of the first medical object based on the first location information;
associating the last-known location and the first medical object in a database; and
providing the last-known location for display at the display device responsive to the tracking request.

12. The method of claim 11,
wherein the first medical object is a medication, and the database is configured to store order status information and an identifier associated with the medication,
wherein the tracking request includes at least a patient's name and the identifier, and wherein the method further comprises:
    determining whether the first medical object is delivered to a delivery location within a time of a predetermined time interval;
    storing the last-known location as the delivery location and a time that the first medical object was delivered to the delivery location in the database; and
    updating the order status information with the last-known location.

13. The method of claim 11, wherein identifying the medical identification information comprises:
    receiving a first indication that the medical identification information was read at the first location when the medical package associated with the first medical object was read at the first location by the reader device, the reader device being configured to wirelessly read the medical identification information from the medical package when the medical package is within a range of the reader device.

14. The method of claim 11, wherein identifying the medical identification information comprises:
    providing delivery progress information comprising a delivery time and an identification of a delivery person associated with delivering the first medical object to the last-known location.

15. The method of claim 11, providing the last-known location for display at the display device comprises:
    providing an interface identifying the first medical object and listing read locations associated with the first medical object, each read location presented with a time at which the first medical object was read at the read location.

16. The method of claim 15, wherein listing the read locations associated with the first medical object comprises:
    presenting, via the interface, each read location juxtaposed on a map of a healthcare facility, each read location identifying on the map where the first medical object was read.

17. The method of claim 15, further comprising:
    causing a mobile device to present the interface and the last-known location.

18. The method of claim 11, wherein providing the last-known location for display at the display device comprises:
    providing the last-known location for display together with an identification of a patient to which the first medical object is assigned.

19. The method of claim 11, further comprising:
    determining, based on receiving the medical identification information and the first location information, that the first medical object is on a mobile carrier with a second medical object;
    receiving, after determining that the first medical object is on the mobile carrier, an indication that the second medical object was delivered to a second location prior to a delivery of the first medical object to a delivery location of the first medical object; and
    determining, based on receiving the indication, that the second location is the last-known location of the first medical object.

20. A non-transitory computer-readable medium comprising instructions stored thereon that, when executed by a dispensing device, cause the dispensing device to perform operations comprising:
    receiving, via a tracking interface of the dispensing device, a tracking request for a delivery status of a first medical object, the tracking interface comprising a display device, and the dispensing device comprising a lockable storage configured to store medical items;
    identifying medical identification information that was read at a first location when a medical package associated with the first medical object was read at the first location by a reader device;
    identifying first location information associated with the first location and the medical package based on the tracking request;
    generating, responsive to receiving the tracking request and identifying the first location information, a last-known location of the first medical object based on the first location information;
    associating the last-known location and the first medical object in a database; and
    providing the last-known location for display at the display device responsive to the tracking request.

21. The non-transitory computer-readable medium of claim 20,
    wherein the first medical object is a medication, and the database is configured to store order status information and an identifier associated with the medication,
    wherein the tracking request includes at least a patient's name and the identifier, and
    wherein the operations further comprise:
        determining whether the first medical object is delivered to a delivery location within a time of a predetermined time interval;
        storing the last-known location as the delivery location and a time that the first medical object was delivered to the delivery location in the database; and
        updating the order status information with the last-known location.

22. The non-transitory computer-readable medium of claim 20, wherein identifying the medical identification information comprises:
    receiving a first indication that the medical identification information was read at the first location when the medical package associated with the first medical object was read at the first location by the reader device, the reader device being configured to wirelessly read the medical identification information from the medical package when the medical package is within a range of the reader device.

23. The non-transitory computer-readable medium of claim 20, wherein identifying the medical identification information comprises:
    providing delivery progress information comprising a delivery time and an identification of a delivery person associated with delivering the first medical object to the last-known location.

24. The non-transitory computer-readable medium of claim 20, providing the last-known location for display at the display device comprises:
    providing an interface identifying the first medical object and listing read locations associated with the first medical object, each read location presented with a time at which the first medical object was read at the read location.

25. The non-transitory computer-readable medium of claim 24, wherein listing the read locations associated with the first medical object comprises:
    presenting, via the interface, each read location juxtaposed on a map of a healthcare facility, each read location identifying on the map where the first medical object was read.

26. The non-transitory computer-readable medium of claim 24, the operations further comprising:
   causing a mobile device to present the interface and the last-known location.

27. The non-transitory computer-readable medium of claim 20, wherein providing the last-known location for display at the display device comprises:
   providing the last-known location for display together with an identification of a patient to which the first medical object is assigned.

28. The non-transitory computer-readable medium of claim 20, the operations further comprising:
   determining, based on receiving the medical identification information and the first location information, that the first medical object is on a mobile carrier with a second medical object;
   receiving, after determining that the first medical object is on the mobile carrier, an indication that the second medical object was delivered to a second location prior to a delivery of the first medical object to a delivery location of the first medical object; and
   determining, based on receiving the indication, that the second location is the last-known location of the first medical object.

* * * * *